United States Patent [19]

Block

[11] Patent Number: 5,719,063

[45] Date of Patent: Feb. 17, 1998

[54] MULTIPLEX IMMUNOASSAY SYSTEM

[75] Inventor: Myron J. Block, Salem, N.H.

[73] Assignee: Boehringer Mannheim Corporation, Indianapolis, Ind.

[21] Appl. No.: 222,113

[22] Filed: Apr. 4, 1994

Related U.S. Application Data

[63] Continuation-in-part of Ser. No. 785,141, Oct. 29, 1991, abandoned, which is a continuation of Ser. No. 398,621, Aug. 25, 1989, abandoned.

[51] Int. Cl.$^6$ ................................................ G01N 33/53
[52] U.S. Cl. .................... 436/501; 436/518; 436/536; 436/537; 436/538; 435/973; 435/967
[58] Field of Search ........................ 435/962, 963, 435/967, 973; 436/56, 172, 501, 518, 536, 537, 538, 807, 825; 422/82.08, 82.11

[56] References Cited

U.S. PATENT DOCUMENTS 4,582,809   4/1986   Block et al. ........................ 436/527

*Primary Examiner*—Toni R. Scheiner
*Attorney, Agent, or Firm*—Lahive & Cockfield, LLP

[57] ABSTRACT

Disclosed is a method of assaying and apparatus for assaying, in assay apparatus, for an analyte in a sample by specifically binding the analyte to a binding molecule having a detectable tag to form a complex, the presence of which can be determined quantitatively by measuring the amount of tag. In one embodiment, the sample is contacted in that apparatus with a complex of binding molecules so as to effect the specific binding. The complex has at least two differently tagged different binding molecules in a predetermined ratio, at least a first of which tagged binding molecules being that which will specifically bind to the analyte. The second tagged binding molecule is one which will not specifically bind to the analyte or to other moieties in the sample. The relative non-specific binding characteristics of those binding molecules with respect to said apparatus are in a known or predetermined relationship. Quantitative measurement of those tags coupled to bound quantities of the binding molecules is then made substantially simultaneously. From the known proportion of binding molecules in the test body, the known ratio between the non-specific binding characteristics of the binding molecules to the apparatus, and the quantitative measurement of the bound tags, one can relatively and accurately determine the specific binding of the first binding molecule to the analyte.

16 Claims, 1 Drawing Sheet

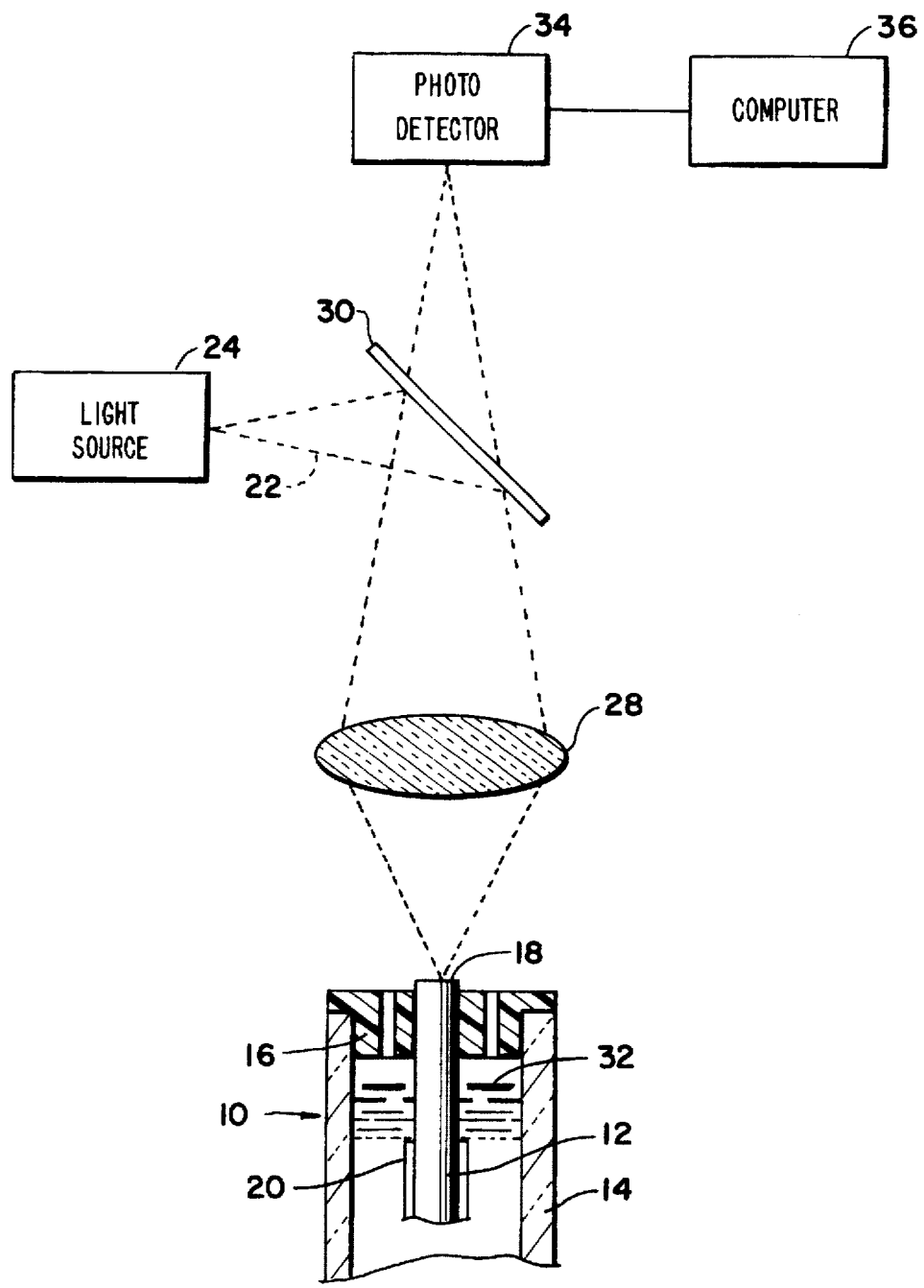

MULTIPLEX IMMUNOASSAY SYSTEM

REFERENCE TO RELATED APPLICATION

This application is a Continuation-in-Part of U.S. patent application Ser. No. 07/785,141 entitled "Multiplex Immunoassay System", filed Oct. 29, 1991, now abandoned, which is a continuation of U.S. patent application Ser. No. 07/398,621 also entitled "Multiplex Immunoassay System" filed Aug. 25, 1989, now abandoned, the disclosures of which are incorporated herein by reference.

This invention relates to chemical and biochemical assays involving one or more binding molecules that will specifically bind to respective reactive moieties of interest, and more particularly to multiplex assays of that type.

Immune reactions involving the formation of antibody-antigen complexes are exemplary of known chemical or biochemical analyte binding molecule reactions in which a complex is formed by the reaction of moieties that will highly specifically bind to one another. A number of other such reactions are known, for example, nucleic acid hybridizations, enzyme-inhibitor, enzyme-coenzyme, hormone-receptor, enzyme-receptor and like substrate-specific reactions. The term "analyte" is intended to refer to the moiety being assayed, either qualitatively, quantitatively or both, and the term "captor" is intended to refer to the binding molecule or moiety that will specifically bind to the analyte of interest.

Assays based upon these well known immune and other specific binding reactions involve a wide variety of techniques. Some assay methods employ radioactive, luminescent or fluorescent tags that are coupled to either the binding molecule or to the analyte, and can be detected by measuring radiation arising from the reaction product or complex. Typically, where a captor such as an antibody immobilized on a substrate is reacted in a solution containing an unknown quantity of a reactant moiety or analyte such as an antigen intended to bind to the captor, the titer of the antigen can be obtained easily. For example, in the well-known competition assay technique, a mixture of the analyte and a known amount of tagged analyte are applied to the immobilized phase and will compete with each other for the binding sites on the binding molecule. The greater the amount of the sample analyte present, the less will be the extent to which tagged analyte will bind to the captor. Using predetermined calibration curves and measuring the intensity of the radiation from the tagged antigen complexed with the bound captor, one can determine or assay the amount of untagged or sample analyte.

In another common technique, one may add the test solution containing analyte to a captor in solution. Assuming that the complex formed will aggregate sufficiently to precipitate or agglutinate, observation of such resulting agglutination or precipitation reaction would indicate whether or not the test solution contained the analyte for which the captor is specific. In the latter case, the observation would be of radiation either reflected or scattered from the agglutinate or precipitate, or radiation the transmission of which is attenuated by the agglutinate or precipitate.

In immunoassays in which radiation (e.g., alpha radiation, luminescent radiation or fluorescent radiation) arises from the reaction product, one may detect and/or measure the radiation typically with Geiger or scintillation counters, autoradiography, fluorimeters and the like.

It is postulated that the binding forces involved in antibody-antigen reactions are the combined interaction of electrostatic, hydrogen bond and van de Waals forces, in many ways similar to other specific binding as, for example, that occurs in enzyme-substrate and in forming enzyme-coenzyme complexes, thereby providing a very strong, specific bond. The specificity of such binding reactions is, however, not absolute. Because moieties, particularly labeled antibody, involved in such specific reactions can often bind to other materials, in assays such as immunoassays and captor assays that depend upon the specificity of the binding, the occurrence of such non-specific binding can have adverse effects on the sensitivity and repeatability of the assay. It will be apparent that the term "bound" as used herein is thus intended to refer to moieties that are bound through any type of binding, specific or non-specific.

Prior art attempts to overcome the effects of non-specific binding on assays have been primarily chemical and are directed to the use of reagents containing proteins that are intended to suppress or block non-specific binding. Such reagents, however, are not universally effective, as reflected by the fact that many different kinds of blockers (e.g., fetal calf serum, gelatin, casein, etc.) have been used in antibody-antigen assays.

In the discussion hereinafter, for the sake of convenience, assays involving specific binding reactions will be exemplified by reference to immunoassays, it being, however, understood that the principles involved, unless specifically noted, can apply to other types of assays involving specific binding reactions.

Achieving the ultimate sensitivity of measurement involving a specific binding reaction is not a matter of having the most powerful signal and the most sensitive instrumentation. Some sensitivity cannot be improved through improvements in the tag and instrument because of the limits imposed by antibody affinity.

For example, consider a capture or noncompetitive immunoassay. In principle, the latter has a potential for greater sensitivity than a competitive immunoassay because the effects of low antibody affinity can be overcome by an increase in the concentration of labeled antibody. The potential sensitivity advantage of a noncompetitive method over a competitive method, using the same antibody in each, increases with the decreasing affinity of the antibody. Using an antibody affinity of $10^{12}M$, if, for example, the effect of non-specific binding can be reduced from 1% to 0.01%, the potential assay sensitivity would go up from $10^5$ to $10^3$ molecules/ml. Increasing the amount of labeled antibody, however, would be accompanied by an increase in the absolute amount of non-specific binding of the labeled antibody, reducing the ability to distinguish the smaller amounts of antigen, and may eliminate or reduce the actual sensitivity advantage of a noncompetitive method.

In a conventional approach in binding pair measurements, non-specific binding is usually estimated by first making a series of external measurements (i.e., apart from or preliminary to the actual measurement of the binding) for the zero response of the instrument system being used. Normally, these external measurements are performed by assay of a sample known to contain none of the analyte of interest. In general, such measurements are not constant but fluctuate about some average value. From such series of measurements, one can define an average non-specific binding (NSB) response and an NSB noise level where the root-mean-square (RMS) noise in the NSB measurements is equal to the standard deviation of the NSB responses. In subsequent assays of unknown analyte concentration, the specific response can then be taken as the system response minus the average NSB response. Of course, in order to be certain that a given sample contains analyte, it is necessary that the specific response be greater than the noise. At very small analyte levels, the noise is usually dominated by the NSB noise.

Accordingly, a principal object of the present invention is to provide a binding pair measurement system that employs an "internal" reference that can be used to supplement "external" control measurements to improve the sensitivity of the system.

Yet another important object of the present invention is to provide such a system in which the effects of non-specific binding of labeled binding molecules such as antibody, are suppressed or minimized, thereby increasing the sensitivity of the assay beyond that presently achievable by prior art immunoassay systems.

Other objects of the present invention will in part be obvious and will in part appear hereinafter.

The invention accordingly comprises the apparatus possessing the construction, combination of elements and arrangement of parts, and the method comprising the several steps and the relation of one or more of such steps with respect to each of the others, all of which are exemplified in the following detailed disclosure, and the scope of the application of which will be indicated in the claims.

BRIEF DESCRIPTION OF THE DRAWING

For a fuller understanding of the nature and objects of the present invention, reference should be made to the following detailed description taken in connection with the accompanying drawing wherein there is shown an idealized, partly schematic, partly cross-sectional view of apparatus embodying the principles of the present invention.

The system of the present invention generally comprises a multiplex assay system in which signals proportional to the extent of binding from two different binding molecules in the system are made and evaluated in real time, typically contemporaneously, i.e., either substantially simultaneously or in a sequence of observations or measurements taken within a comparatively short time with respect to the same sample under assay. It is preferred in most instances to make the observations as nearly simultaneously as possible to reduce any effects of fast changes in background.

The multiplex system of the present invention should be distinguished from known multichannel assays in which two or more analytes are substantially simultaneously assayed using different labeled binding molecules that will respectively uniquely specifically bind to the corresponding analytes. Cf. A Dual Radioimmunoassay for the Detection of Morphine and Cocaine in Urine, A. S. Young, F. Rubio and S. E. Wagner, *Clinical Chemistry*, Vol. 34, No. 6, 1988, p. 1161.

A typical embodiment of the multiplex assay system of the present invention, however, is one that determines the specific binding reaction with a specific analyte of interest in a sample, in which system two or more differently labeled binding molecules, each with its own different binding characteristics, are contemporaneously observed with respect to the sample in the system. The responses obtained are processed to reduce the effects of non-specific binding in such assay, so that the specific binding response can be more accurately determined.

The method of the present invention, therefore, provides for an assay for an analyte of interest in a sample. The method comprises the step of providing at least two different binding molecules each coupled to a respective different type of tag distinguishable one from the other, with only the first of such binding molecule being capable of specifically binding with that analyte. The binding molecules and the sample are contacted with one another, as by mixing, to form a including a complex (which may be a liquid volume) involving at least that first binding molecule and the analyte. Measurement is then made contemporaneously, quantitatively and separately of such of each of the tags as are coupled only to bound binding molecules in the complex, and those measurements are compared. Measurements, of course, can be more easily made by first segregating the bound from the unbound binding molecules, e.g., as by washing the unbound binding molecules away.

The present invention is embodied in apparatus for assaying for the analyte in the sample by specifically binding the analyte to an immobilized binding molecule on a reaction surface to form a complex. Specific binding is effected by contacting the sample with the immobilized binding molecule and a different and differently tagged second binding molecule. The two different binding molecules are provided in predetermined proportion to one another, and are not cross-reactive with each other. Preferably the second binding molecule will not specifically bind to the analyte or to other moieties in the sample. The different tags on the binding molecules can be measured quantitatively. The relative non-specific binding characteristics of those binding molecules with respect to the apparatus are in a known or predetermined function or relationship. Quantitative measurement of those tags coupled only to bound quantities of the binding molecules is then made substantially contemporaneously. From the known proportion of binding molecules in the test body, the known relationship between the non-specific binding characteristics of the binding molecules to the apparatus, and the quantitative measurement of the bound tags, one can relatively accurately determine the specific binding of the first binding molecule to the analyte.

Particularly, the different tags are selected so that they can respectively provide signals that are readily distinguishable from one another, e.g., fluoresce at different wavelengths. Thus, the quantitative measurements made separately are of the amplitude of the signals provided from the excited tags that are coupled to those binding molecules which are both specifically and non-specifically bound in the course of the assay. Because the relative proportion of binding molecules to one another in the complex or reagent is known, and because also the relationship between the non-specific binding characteristics of those binding molecules with respect to the assay apparatus is also known or predetermined, it becomes relatively simple for one to then determine in real time the extent to which the signals measured are due to the specifically bound binding molecules.

For example, assume that binding molecule ($B_s$), which will specifically bind to the analyte, and binding molecule ($B_n$), which will not specifically bind to the analyte, are present in a ratio ($R_1$) of 1:1 in the complex. Further assume that pretesting of the reagent in the assay apparatus in the absence of any of the analyte of interest has established that the binding molecules will bind non-specifically in the ratio ($R_2$) of 1:2 ($B_s$:$B_n$). The assay then requires that the sample with the analyte of interest, if any, is contacted with the binding molecules. This will result in both the specific binding of the analyte and $B_s$, and the non-specific binding of the binding molecules to the assay apparatus (which term in this context should be understood to include any binding reactions that occur other than the specific binding of the analyte to $B_s$). Simultaneous measurement is then made of the distinctive and separate signals (i.e., separate channel measurements) from the respective tags on the bound binding molecules. In an idealized case, the signals from $B_n$ will be due only to binding molecule $B_n$ that was non-specifically bound whereas the signals from $B_s$ will arise from binding molecules that are both specifically and non-specifically bound. Because it is known that the binding molecules were present in ratio $R_1$ and the relative non-specific binding characteristics of those binding molecules in the reagent was $R_2$, then one can employ these relationships to determine the extent of the signal that arose from specifically bound $B_s$.

For example, assume that the amplitudes of the signals are measured at $A_s$ and $A_n$, representing respectively the specifically and non-specifically bound $B_s$ and the non-specifically bound $B_n$, then the portion S of the signal $A_s$ due only to the specifically bound $L_s$ can be expressed as:

$$S = A_s - A_n f(R_1, R_2) \qquad (1)$$

where $f(R_1, R_2)$ is a function (not necessarily either linear or non-linear) of the values $R_1$ and $R_2$.

A simple exemplary form of the function as a product is:

$$f = k_1 R_1 k_2 R_2 \qquad (2)$$

where $k_1$ and $k_2$ are simply proportionality or weighting constants to be determined empirically. A variation on the present invention is embodied in assay apparatus as described above, but one in which, additionally there is employed yet another or third binding molecule tagged with a tag that can be measured quantitatively, can be differentiated readily from the tags on the other two binding molecules, and will specifically bind to either a different site on the analyte of interest or to a different analyte. All three binding molecules are, of course, in a predetermined proportion to one another, and the binding molecules are not cross-reactive. The relative non-specific binding characteristics of those three binding molecules with respect to the apparatus are in a known or predetermined function or relationship. This system then provides three channels, e.g., two specific channels and one non-specific channel, from which the specific binding characteristics of the specifically-binding binding molecules can be determined.

One embodiment of the present invention can advantageously be described in a context of a fluorescent immunoassay system employing fluorescent tags, particularly an assay employing attenuated total reflection (ATR) cells, but it is to be understood that the principles of the invention extend to other types of assays involving specific binding reactions and employing other types of detectable tags.

The use of an ATR cell in the form of a slab of radiation transmissive material, to observe and measure fluorescence induced at a cell surface by an evanescent wave and traveling across the cell substantially normal to the plane of that cell surface, was first suggested by T. Hirschfeld in U.S. Pat. No. 3,604,927. A more sophisticated ATR immunoassay apparatus is shown and described in detail in U.S. Pat. No. 4,558,014, issued Dec. 10, 1985, and the description of and operation of such an ATR cell is incorporated herein by reference. A distinct advantage is obtained by using such an ATR cell in the present invention because fluorescent signals detected by such a cell arise only within the evanescent zone adjacent the reaction surface of the cell. Thus, the cell, per se, automatically segregates free binding molecules from those binding molecules that are non-specifically bound to the reaction surface and that are specifically bound in complexes formed at the reaction surface.

Referring to the drawing, there is shown a cross-section of a fragment of totally internally reflecting assay cell 10. One preferred embodiment of cell 10 comprises a cylindrical rod or fiber 12 that is an elongated, substantially cylindrical, optically transparent body. This body is adapted to propagate along its length, by multiple total internal reflections, optical radiation entering an end of the fiber within an established solid angle substantially rotationally symmetric about the longitudinal axis of the fiber. By way of example, fiber 12 may be any of a number of optically transparent materials such as glass, quartz, sapphire, polypropylene, polyolefins, nylon and the like, having an index of refraction greater than that of the fluid sample being assayed. As will be described hereinafter, a synthetic polymer is preferred inasmuch as the attachment thereto of a coating hereinafter described can be effected more readily than to an inorganic substrate such as glass. Preferably, fiber 12 is enclosed within capillary tube 14 formed of a material that is relatively insoluble and non-reactive with the fluid being assayed. Fiber 12 passes through and is supported coaxially within capillary tube 14 typically by stopper 16, thereby disposing all of the fiber except for end face 18 within tube 14.

Disposed on a portion of the outer surface of fiber 12 is an immobilized or prebound coating 20 which, for example, can be formed of one of the reactants of an immune type reaction, i.e., a moiety of an antigen-antibody complex. Typically, coating may be applied by first providing the fiber surface or substrate with a plurality of coupling sites and then a number of the desired moieties of an antibody-antigen complex may be bound to those sites, preferably covalently and in known manner. The coupling sites on the substrate to which the selected moieties of the antigen-antibody complex are initially immobilized are selected so as to provide the requisite immobilization without appreciably affecting the affinity and avidity of the moiety for the complementary portion of the complex. Where fiber 12 is glass, appropriate attachment sites may be provided as is well known, for example, by reacting a silyl compound with the glass surface. Coupling of other suitable silyl compounds, and methods by which carboxyl, amino and other reactive groups of antibody or antigen may be covalently bound to various inorganic materials are described by Weetall in U.S. Pat. No. 3,652,761. Binding to polymers is often easier and there is extensive literature describing the immobilization of antibodies and antigens on the surface of polymers. Coating 24 may also be applied by adsorption, in some instances by simply wetting the cell surface with a suitable reagent having an appropriately selected moiety.

For example, for the well known sandwich assay, the selected moiety to be immobilized on the ATR substrate would be a binding molecule that will bind specifically to the analyte of interest. The binding molecule is preferably provided in sufficient quantity to yield a number of reaction sites well in excess of the number of analyte molecules or moieties to be assayed, so that the reaction sites will not be saturated subsequently. The coated cell would then be contacted with both the sample that may contain the analyte being assayed and the reagent containing the two labeled or tagged binding molecules and the reactants allowed to incubate for a time sufficient to insure that the binding reactions have been substantially completed. Signals obtained from the tagged binding molecules that have bound to the immobilized analyte and have non-specifically bound to other portions of the assay apparatus are then measured. The signal measured from the second bound binding molecule (i.e., that which is not capable of specifically binding to the analyte) can then be used to predict (through a nomogram, table or formula) what amount or proportion of the signal received from the first bound binding molecule arose from the specific binding of the latter to the analyte.

In the ATR system described as exemplary, source 24 is provided for delivering beam 22 of light to cell 10. While source 24 can be a broadband source light such as a condenser illuminated with light from an incandescent lamp, a light-emitting diode, sunlight and the like, it is preferred that source 24 constitutes a dual source to provide excitation radiation within a pair of narrow wavelength bands, and to this end can include appropriate band pass filters. The center wavelengths of the two bands are chosen in accordance with the absorption characteristics of the fluorophors used as the tags on the labeled binding molecule, so as to excite the latter into fluorescence when illuminated. Light source 24 also includes appropriate beam shaping means, as understood by those skilled in the art, to illuminate objective lens 28 with a beam of appropriate vergence so as to permit lens 28 to image the source aperture on end face 18, preferably with no ray incident on face 18 at an angle greater than that corresponding to the numerical aperture of the fiber.

In a preferred embodiment, beamsplitter 30 is interposed between source 24 and lens 28 and is formed so as to reflect the two excitation wavelength bands and transmit the respective fluorescent emissions from face 18.

If the sample containing analyte is introduced into interspace 32 between fiber 12 and tube 14, the analyte will react with the immobilized binding molecule in coating 20 assuming that the binding molecule has been selected to specifically bind to that analyte and some of the analyte is present in the sample. If now, to perform a sandwich assay, one introduces the two differently labeled different binding molecules into interspace 26, the first labeled binding molecules will specifically bind both to free analyte and to analyte that had been bound to the immobilized binding molecules. Removal of non-immobilized binding molecules from the reaction zone will leave immobilized specific and non-specific bound binding molecules. The second labeled binding molecules will not specifically bind to the analyte, but can be expected to non-specifically bind to the surface of fiber 12 as some of the first labeled binding molecules will also do.

Upon introducing a light beam from source 24 at an appropriate angle into face 18 of fiber 12, the beam will propagate through the fiber by total internal reflection, creating an evanescent wave in an evanescent zone (not shown) contiguous with the fiber surface. The evanescent wave, where incident on such bound binding molecules, will cause the labels or tags to fluoresce at two different wavelengths (read by two different channels), and a large part of that fluorescence will be directed or tunneled back into the medium of fiber 12, some at or above the critical angle and some below the critical angle. Light directed back into the cell at or above the critical angle will be propagated through fiber 12, some emerging from input face 18.

Measurement of the respective amplitudes of the two different wavelengths of fluorescent light emergent from face 18 by electrooptical detection means 34 will indicate the respective quantitative presence of the bound binding molecules. To this end means 34 may comprise two electrooptical detectors respectively sensitive to the respective wavelengths. Alternatively, one may also employ, in lieu of source 24 and detection means 34, a fluorimeter having switchable excitation and emission filters respectively appropriate to the excitation and detection of emission from the corresponding tags. Such measurements of the amplitudes of the signals from the tags, together with the other predetermined information regarding the values of $R_1$ and $R_2$, can then be fed into means 36, such as an appropriately programmed digital computer or a properly hard-wired circuit, to make the desired determination, as described above, of the extent of the specific binding achieved.

The utility of a multiplex system for determination of non-specific binding in the presence of specific binding was shown in a test system exemplified in the following detailed example. The test reagent was formed of goat antibovine IgG (as the first binding molecule expected to specifically bind to bovine IgG) labeled with fluorescein in known manner, and of goat antimouse IgG (as the second binding molecule) labeled with rhodamine in known manner. The ATR cell, a polystyrene-coated quartz fiber, was coated, at least in a reaction zone on its surface, with bovine IgG for the test systems and was kept uncoated in the control systems. These reagents were obtained from Jackson Immunological Corporation and the antibodies were prescreened by the supplier for cross-reactivity.

A preliminary determination of the non-specific binding of both antibodies was first made with respect to a number of substantially identical bare, polystyrene-coated quartz fibers by first incubating the latter in phosphate-buffered saline (PBS) solution (pH 7.4) obtained from Sigma Chemical. After incubation, each of the fibers was placed in a flow cell in an ATR fluorimeter having a pair of detector channels respectively responsive to the major wavelengths of fluorescein and rhodamine respectively (530 nm and 580 nm). A preferred embodiment employs a fluorimeter having switchable excitation and emission filters respectively appropriate to the excitation and detection of fluorescence from fluorescein and rhodamine, i.e., excitation filters 480/20 (480 nm center wavelength, 20 nm bandpass) for fluorescein and 530/30 for rhodamine; fluorescence filters of 530/30 for fluorescein and 580/20 for rhodamine.

Each fiber was washed in flowing PBS for two minutes. Flow was stopped, excitation light (480 and 530 nm in sequence) of fixed intensity was introduced into the fiber at one end, and background readings (in mV) were recorded for each of the two channels, one reading the background in the fluorescein detection channel and one in the rhodamine detection channel. The PBS was then flushed from the flow cell and replaced with a flow of solution of equal volumes of 7.5 ug/ml rhodamine-labeled antimouse IgG and 7.0 ug/ml fluorescein-labeled antibovine IgG. Flow was stopped and the fiber allowed to incubate for two minutes at room temperature. The antibody solution was then washed out with a flow of PBS for four minutes. The same excitation light was again introduced into the fiber and readings (in mV) representing the sum of the respective backgrounds and the non-specific binding were taken to obtain values of $A_f$ and $A_r$ for the fluorescein and rhodamine channels, respectively, for four such fibers.

The data are summarized in the following Table A in which $A_f$ and $A_r$ are respectively the amplitude in mV of the signals received from the bound fluorescein and rhodamine-labeled IgG. "Pre-inc." and "post-inc." refer to the signals measured respectively prior to incubation and after incubation and wash. The binding response is simply the difference between the pre-inc. and post-inc. respective signals, and the binding ratio is the ratio of the binding responses.

TABLE A

| System Response | | | | | | |
|---|---|---|---|---|---|---|
| Pre-inc. | | Post-inc. | | Binding Response | | Binding Ratio |
| $A_f$ | $A_r$ | $A_f$ | $A_r$ | $A_f$ | $A_r$ | Fluor/Rhod. |
| 303 | 297 | 712 | 651 | 409 | 354 | 1.155 |
| 398 | 492 | 1170 | 1080 | 772 | 588 | 1.313 |
| 338 | 322 | 744 | 668 | 406 | 346 | 1.173 |
| 397 | 355 | 895 | 764 | 498 | 409 | 1.218 |

Note that the average binding ratio was 1.215 with a standard deviation of 0.070 and a C.V. of 5.798%. The average NSB response for $A_r$ was 521 mV with a standard deviation of 172.5 mV (C.V. 33%), which in effect is a measure of the noise at zero analyte level.

The foregoing responses were, of course, made of surfaces that were bare of antigen. It will be appreciated, however, that one can make a similar series of measurements on a fiber blocked with a protein or some other blocking agent that is not specifically bound by either of the antibodies. Using such blockers should serve to reduce possible unwanted effects due to differences in the non-specific binding characteristics of the antibodies with regard to blocked and bare fibers respectively.

The same mixture of antibodies was then reacted with five of the identical fibers as previously used. The same procedure as described was followed except that the fibers were prepared by incubation for five minutes in 0.5 ug/ml bovine IgG rather than by incubation in PBS. The results of the example are shown in Table B.

TABLE B

| System Response | | | | | |
|---|---|---|---|---|---|
| Pre-inc. | | Post-inc. | | Binding Response | |
| $A_f$ | $A_r$ | $A_f$ | $A_r$ | $A_f$ | $A_r$ |
| 729 | 501 | 1650 | 1183 | 921 | 682 |
| 568 | 435 | 1508 | 987 | 940 | 552 |
| 478 | 457 | 1355 | 1030 | 877 | 573 |
| 420 | 322 | 722 | 569 | 302 | 247 |
| 542 | 502 | 1530 | 1161 | 988 | 659 |

From this latter data it can be determined that the specific response provided by the fluorescein-labeled IgG was the total average binding ratio minus 1.215 (the predetermined binding ratio found from Table A) times the average $A_r$. This yields an average binding response of 146.2 mV with a standard deviation of 102 mV.

The prior art conventional method of data analysis is to take the average $A_f$ value from Table B and subtract from it the average $A_f$ value due only to the non-specific binding as shown as the average $A_f$ in Table A. Following this method, the average specific binding response is 284.6 mV and the standard deviation is 284.3 mV. A convenient method of comparison of the prior art and the method of the present invention is to determine the average signal-to-noise ratio (S/N) at the analyte level used. According to the prior art method then, the S/N is 284.6/284.3 or 1.00, where the method of the present invention gives a S/N of 146.2/102 or 1.43. This constitutes an improvement in S/N of about 1.5 at the analyte level chosen and a reduction in the noise by a factor of about 2.8 in the zero analyte response.

Another example of multiplex apparatus of the present invention being used to determine NSB can be seen from the following. It is known that a virus may elicit the formation of more than one type of antibody, e.g., two different antibodies respectively specific to the envelope and to the core of the virus. For diagnostic purposes, one may wish to assay a sample, for example of blood, suspected of containing the antibodies to a specific type of such virus.

Consequently, one can immobilize lysate of that virus, for example, as a coating on the surface of an optical fiber, applied as by adsorption. That coated fiber is then contacted with that sample, thereby forming complexes by specifically binding the lysate fragments of core and envelope with any respective corresponding antibodies that may be present in the sample. A reagent is prepared containing a known ratio of first and second synthetic or natural proteins respectively corresponding to the envelope and core proteins of the virus and respectively labeled with fluorescent tags such as fluorescein and rhodamine in known manner. The reagent is mixed with the sample and the coated fiber so that the proteins in that reagent can also specifically bind to those antibodies earlier bound to the lysate coating, and non-specifically bind elsewhere to the fiber.

The specific binding ratio of the two proteins is determined by the ratio of the binding sites provided by the relative amounts of two antibodies present in the sample and bound to the coating. If there is a prior knowledge of the ratio of such binding sites, then the reagent is prepared with a ratio of proteins that is markedly different than the ratio of binding sites.

The labeled proteins bound to the fiber are now separately and substantially simultaneously excited into fluorescence in the apparatus of the present invention, providing signals produced by a combination of specific and non-specific binding of the tagged proteins. It will be apparent, however, that the ratio of the respective signals produced by the tags on proteins that are specifically bound corresponds to the ratio of the binding sites, but the ratio of the signals produced by tagged proteins that are non-specific bound will correspond to the known ratio at which the respective proteins are supplied in the reagent. Where the ratio of binding sites or antibodies is also known then, because the two ratios differ considerably (being under the control of the preparer of the reagent), the amplitudes of the respective signals can be correspondingly adjusted to remove the effect of the non-specific binding.

If there is no a prior knowledge of the ratio of binding sites, i.e., the ratio of antibodies, one can perform a preliminary assay using another reagent in which the proteins are present in a first ratio, e.g., unity. Using the results of that assay, a second assay is then performed with a second reagent in which the ratio of proteins has been established, for example, as the inverse of the measurement of the signals in the first assay. The measurement of signals in the second assay supplies sufficient information from which one can make calculations that will separate out the effects of non-specific binding.

Since certain changes may be made in the above method and apparatus without departing from the scope of the invention involved, it is intended that all matter contained in the above description or shown in the accompanying drawing shall be interpreted as illustrative and not in a limiting sense.

What is claimed is:

1. A method for assaying for an analyte of interest in a sample, said method comprising the steps of:
   providing at least two different binding molecules each coupled to a respective different type of tag distinguishable one from the other to an analysis system, at least a first of said binding molecules being capable of specifically binding with said analyte and at least a second of said binding molecules not being capable of specifically binding with said analyte;

contacting said binding molecules and said sample to form a complex involving at least said first binding molecule and said analyte;

quantitatively and separately measuring the distinguishable characteristics of said tags attached to said first binding molecules and said second binding molecules, said measurement of said first tag providing a measure of bound analyte and said measurement of said second tag providing a measure of nonspecific binding in said system; and comparing the measurements of said tags to determine the specific binding of said first binding molecule with respect to said analyte such that said analyte is assayed.

2. The method as defined in claim 1 including the steps of:

providing said first and second tagged different binding molecules in a predetermined proportion to one another;

determining a correlation between the non-specific binding characteristics of said binding molecules with respect to said system;

contacting said binding molecules with said sample in said system so as to effect said specific binding and form said complex; and determining the specific binding of said first binding molecule with respect to said analyte from said predetermined proportion, said correlation and the comparison of said measurements.

3. The method as defined in claim 2 including the step of segregating, after said contacting step, substantially all of said analyte and binding molecules which are not bound from those binding molecules which are bound to said analyte and said system.

4. The method as defined in claim 3 Wherein each of said different tags, when excited, can respectively provide signals distinguishable from one another, and said measurements are of the amplitude of said signals from substantially only the bound binding molecules.

5. The method as defined in claim 4 wherein each of said different tags, when excited, provides fluorescent radiation at wavelengths that differ from one another.

6. The method as defined in claim 2 in which the second of said binding molecules will not specifically bind to said analyte or to other moieties in said sample.

7. The method as defined in claim 6 wherein said first binding molecule is provided in excess of the amount expected to specifically bind with said analyte in said sample.

8. The method as defined in claim 4 including the step of determining said correlation by:

preliminary assaying said binding molecules in said system in the absence of said analyte so as to quantitatively measure the amplitudes of the respective signals from said tagged binding molecules that become non-specifically bound during the preliminary assay; and determining the ratio of the measured signal amplitudes from said first binding molecule and said second binding molecules.

9. The method as defined in claim 4 wherein said step of determining is carried out by modifying, in accordance with a function of said predetermined proportion and said known correlation, the value of the signal from said second binding molecules to thereby provide a modified value, and comparing to said modified value the amplitude of the signal from said first binding molecule.

10. The method as defined in claim 4 wherein said step of determining is carried out by subtracting from the amplitude of the signal from said first binding molecule, the product of said correlation times said predetermined proportion times the amplitude of the signal from said second binding molecules.

11. Apparatus for assaying a solution for an analyte of interest, said apparatus comprising, in combination:

at least two differently tagged binding molecules each labeled differently with respective tags, the presence of which tags can be quantitatively determined, at least a first of said binding molecules being capable of specifically binding to said analyte and at least a second of said binding molecules not being capable of specifically binding with said analyte;

a reaction surface at which at least said first binding molecule can form a specifically-bound complex with said analyte;

means for contemporaneously quantitatively and separately measuring such of each of said tags as may be bound at said surface such that said measurement of said first tag provides a measure of bound analyte and said measurement of said second tag provides a measure of nonspecific binding in said apparatus; and means for comparing the measurement of said tags to determine the specific binding of said first binding molecule with respect to said analyte.

12. The apparatus as defined in claim 11 wherein said first binding molecule is immobilized on said reaction surface.

13. The apparatus as defined in claim 11 wherein said reaction surface is a surface of an attenuated total reflection cell.

14. The apparatus as defined in claim 13 including means for introducing radiation into said cell at wavelengths capable of exciting both of said tags into emitting respective different signals.

15. The apparatus as defined in claim 14 wherein said means for contemporaneously quantitatively and separately measuring comprises a pair of detectors each respectively sensitive to one of said respective different signals.

16. The apparatus as defined in claim 14 wherein said means for contemporaneously quantitatively and separately measuring comprises a fluorimeter having switchable excitation and emission filters respectively appropriate to the excitation and detection of emission from said tags.

* * * * *